(12) United States Patent
Morris et al.

(10) Patent No.: US 9,422,592 B2
(45) Date of Patent: Aug. 23, 2016

(54) SYSTEM AND METHOD OF DETECTING RNAS ALTERED BY CANCER IN PERIPHERAL BLOOD

(71) Applicant: VIOMICS Inc., Phoenix, AZ (US)

(72) Inventors: Scott Morris, Phoenix, AZ (US); David Mallery, Solana Beach, CA (US)

(73) Assignee: VIOMICS, INC., Phoenix, AZ (US)

( * ) Notice: Subject to any disclaimer, the term of this patent is extended or adjusted under 35 U.S.C. 154(b) by 0 days.

(21) Appl. No.: 13/734,735

(22) Filed: Jan. 4, 2013

(65) Prior Publication Data

US 2013/0196332 A1    Aug. 1, 2013

Related U.S. Application Data

(60) Provisional application No. 61/584,097, filed on Jan. 6, 2012.

(51) Int. Cl.
    *C12Q 1/68*    (2006.01)

(52) U.S. Cl.
    CPC ............. *C12Q 1/68* (2013.01); *C12Q 1/6886* (2013.01); *C12Q 2600/158* (2013.01)

(58) Field of Classification Search
    CPC ........... C12Q 1/6886; C12Q 2545/113; C12Q 2600/118; C12Q 2600/158
    See application file for complete search history.

(56) References Cited

U.S. PATENT DOCUMENTS

| | | | |
|---|---|---|---|
| 5,475,610 A | 12/1995 | Atwood et al. | |
| 5,538,871 A | 7/1996 | Nuovo et al. | |
| 5,602,756 A | 2/1997 | Atwood et al. | |
| 5,612,743 A | 3/1997 | Lee | |
| 6,040,139 A | 3/2000 | Bova | |
| 6,100,051 A | 8/2000 | Goldstein et al. | |
| 6,329,179 B1 | 12/2001 | Kopreski | |
| 6,916,634 B2 | 7/2005 | Kopreski | |
| 6,939,671 B2 | 9/2005 | Kopreski | |
| 7,709,233 B2 | 5/2010 | Kopreski | |
| 7,732,141 B2 | 6/2010 | Kopreski | |
| 7,767,390 B2 | 8/2010 | Kopreski | |
| 7,767,422 B2 | 8/2010 | Kopreski et al. | |
| 7,767,423 B2 | 8/2010 | Kopreski | |
| 7,785,842 B2 | 8/2010 | Kopreski | |
| 7,897,356 B2 | 3/2011 | Klass et al. | |
| 7,932,061 B2 | 4/2011 | Kopreski | |
| 7,968,317 B2 | 6/2011 | Kopreski et al. | |
| 7,972,817 B2 | 7/2011 | Kopreski | |
| 8,030,031 B2 | 10/2011 | Kopreski | |
| 8,043,835 B1 | 10/2011 | Kopreski | |
| 8,148,069 B2 | 4/2012 | Croce et al. | |
| 8,163,524 B2 | 4/2012 | Kopreski | |
| 8,252,538 B2 | 8/2012 | Croce et al. | |
| 2004/0085443 A1 | 5/2004 | Kallioniemi et al. | |
| 2005/0153918 A1 | 7/2005 | Chabot et al. | |
| 2006/0010508 A1 | 1/2006 | Tilly et al. | |
| 2006/0051736 A1 | 3/2006 | Shields et al. | |
| 2006/0199169 A1 | 9/2006 | Lam et al. | |
| 2008/0003571 A1 | 1/2008 | McKernan et al. | |
| 2009/0190820 A1 | 7/2009 | Dela Torre Bueno | |
| 2009/0247416 A1 | 10/2009 | Can et al. | |
| 2010/0291573 A1 | 11/2010 | Cowens et al. | |

FOREIGN PATENT DOCUMENTS

WO    WO 03/74069 A2    9/2003

OTHER PUBLICATIONS

International search Report and Written Opinion for PCT/US2013/020383 dated Apr. 22, 2013.
Silva et al., "Detection of Epithelial Messenger RNA in the Plasma of Breast Cancer Patients is Associated with Poor Prognosis Tumor Characteristics", Clin. Cancer Res. 7(9):2821-2825, Sep. 2001.
Ausubel et al, eds., Current Protocols in Molecular Biology, Greene Publishing and Wiley-Interscience, NY, 1995.
Fedurco et al., BTA, a novel reagent for DNA attachment of glass and efficient generation of solid-phase amplified DNA colonies, Nucleic Acid Research 34, e22, 2006.
Gemperle, C. et al., Regulation of the Formyl Peptide Receptor 1 (FPR1) Gene in Primary Human Macrophages, PLOS One, www.plosone.org, Nov. 2012, vol. 7:11, e50195, pp. 1-6.
Harris, T.D. et al., Single-molecule DNA sequencing of a viral genome, Science 320:106-109, 2008.
Huang, J. et al., Transactivation of the Epidermal Growth Factor Receptor by Formylpeptide Receptor Exacerbates the Malignant Behavior of Human Glioblastoma Cells, Cancer Res 2007; 67:5906-5913. Downloaded from cancerres.aacrjournals.org on Jan. 3, 2013.
Huang, Wen-Yi, Timothy M. Sheehy, Lee E. Moore, Ann W. Hsing and Mark P. Purdue; Simultaneous Recovery of DNA and RNA from Formalin-Fixed Paraffin_embedded Tissue and Application in Epidemiologic Studies; Cancer Epidemiol Biomarkers Prey; Published online Mar. 23, 2010; final publication Apr. 19, 2010: 973.
Mandal, P. et al., Signaling in Lipopolysaccharide-Induced Stabilization of Formyl Peptide Receptor 1 mRNA in Mouse Peritoneal Macrophages, J Immunol 2007; 178:2542-2548.
Mandal, P. et al., Lipopolysaccharide Induces Formyl Peptide Receptor 1 Gene Expression in Macrophages and Neutrophils via Transcriptional and Posttranscriptional Mechanisms, J Immunol, 2005; 175:6085-6091.
Margulies et al, Genome sequencing in microfabricated high-density picolitre reactors, Nature 437:376-380, 2005.
Montgomery, K., et al. "Non-fiducial, shape-based registration of biological tissue," Proceedings-SPIE The International Society for Optical Engineering, 1996, pp. 224-233, Issue 2655.

(Continued)

*Primary Examiner* — David Thomas
(74) *Attorney, Agent, or Firm* — Knobbe Martens Olson & Bear, LLP

(57) ABSTRACT

Analyzing peripheral blood RNA populations presents an effective, accurate, minimally invasive method of determining a patient's cancer status. Using circulating free RNA of the genes disclosed herein, systems and methods are disclosed which can accurately identify cancer signatures in the patient blood samples.

30 Claims, 5 Drawing Sheets

(56) References Cited

OTHER PUBLICATIONS

Figure 1A:
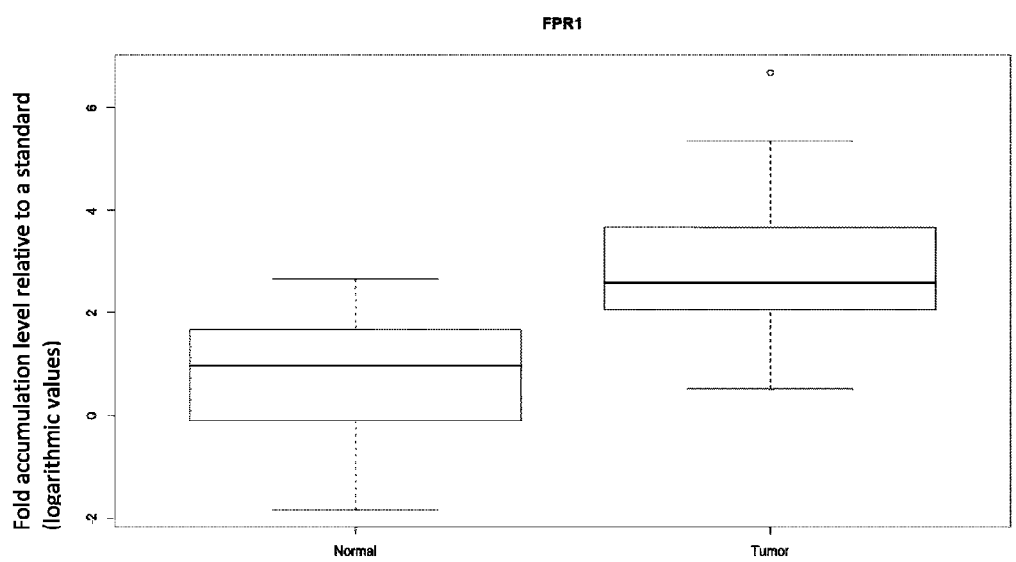

International Search Report and Written Opinion for PCT/US2011/024090, dated Jun. 15, 2011.

nCounter® Analysus System, Product Data Sheet, nanoString® Technologies, v. 20111123, 2012.

Oxford Nanopore Technologies; http://www.nanoporetech.com/technology/the-gridion-system/the-gridion-system.

QIAamp® Circulating Nucleic Acid Handbook, 2nd Edition, Jan. 2011, Sample & Assay Technologies.

Ronaghi et al., Real-time DNA sequencing using detection of purophosphate release, Anal. Biochem, 242:84-89, 1996.

Rothberg et al., An integrated semiconductor device enabling non-optical genome sequencing, Nature 475, 348-352, 2011.

Shao, et al., Formyl Peptide Receptor Ligands Promote Wound Closure in Lung Epithelial Cells, Am J Respir Cell mol Biol, vol. 44, pp. 264-269, 2011.

Shendure, J. et al., Accurate multiplex polony sequencing of an evolved bacterial genome, Science 309, 1728-1732, 2005.

Shendure and Ji, Next-generation DNA sequencing, Nature Biotechnology 26)10): 1135-1145, 2008.

Turcatti et al., A new class of cleavable fluorescent nucleotides: synthesis and optimization as reversible terminators for DNA sequencing by synthesis, Nucleic Acid Research 36, e25, 2008.

Vancompernolle, Scott E. et al., Expression and Function of Formyl Peptide Receptors on Human Fibroblast Cells, J Immunol 2003; 171:2050-2056, http://www.jimmunol.org/content/171/4/2050.

Wang, W. et al., Crosstalk to Stromal Fibroblasts Induces Resistance of Lung Cancer to Epidermal Growth Factor Receptor Tyrosine Kinase Inhibitors, Clin Cancer Res 2009; 15:6630-6638. Downloaded from clincancerres.aacrjournals.org on Jan. 3, 2013.

Rondepierre F. et al., (Jan. 1, 2009), "Proteomic studies of B16 lines: Involvement of Annexin A1 in melanoma dissemination", Biochimica et Biophysica Acta (BBA)—Proteins & Proteomics, Elsevier, Netherlands, vol. 1794, No. 1, pp. 61-69.

Khau T. et al., (Oct. 7, 2010), "Annexin-1 signals mitogen-stimulated breast tumor cell proliferation by activation of the formyl peptide receptors (FPRs) 1 and 2", The FASEB Journal, vol. 25, No. 2, pp. 483-496.

Yang et al., (Sep. 1, 2011), "Annexin 1 Released by Necrotic Human Glioblastoma Cells Stimulates Tumor Cell Growth through the Formyl peptide Receptor 1", American Journal of Pathology, vol. 179, No. 3, pp. 1504-1512.

Extended European Search Report for European Patent Application No. 13733697.0 dated Nov. 4, 2015.

SEQUENCE LISTING

```
<160> NUMBER OF SEQ ID NOS: 12

<210> SEQ ID NO 1
<211> LENGTH: 18
<212> TYPE: DNA
<213> ORGANISM: Homosapiens

<400> SEQUENCE: 1
tgacggtgag aggcatca                                                   18

<210> SEQ ID NO 2
<211> LENGTH: 23
<212> TYPE: DNA
<213> ORGANISM: Homosapiens

<400> SEQUENCE: 2
cggttcatca ttggcttcag cgc                                             23

<210> SEQ ID NO 3
<211> LENGTH: 22
<212> TYPE: DNA
<213> ORGANISM: Homosapiens

<400> SEQUENCE: 3
ggtggcaata agcccataac tg                                              22

<210> SEQ ID NO 4
<211> LENGTH: 18
<212> TYPE: DNA
<213> ORGANISM: Homosapiens

<400> SEQUENCE: 4
aggccaaccg cgagaaga                                                   18

<210> SEQ ID NO 5
<211> LENGTH: 27
<212> TYPE: DNA
```

<213> ORGANISM: Homosapiens

<400> SEQUENCE: 5
tgacccagat catgtttgag accttca    27

<210> SEQ ID NO 6
<211> LENGTH: 22
<212> TYPE: DNA
<213> ORGANISM: Homosapiens

<400> SEQUENCE: 6
tgccatccta aaagccaccc ca    22

<210> SEQ ID NO 7
<211> LENGTH: 21
<212> TYPE: DNA
<213> ORGANISM: Homosapiens

<400> SEQUENCE: 7
gggctttgcc tttgtaacct t    21

<210> SEQ ID NO 8
<211> LENGTH: 23
<212> TYPE: DNA
<213> ORGANISM: Homosapiens

<400> SEQUENCE: 8
tgacgaccat gactccgtgg ata    23

<210> SEQ ID NO 9
<211> LENGTH: 22
<212> TYPE: DNA
<213> ORGANISM: Homosapiens

<400> SEQUENCE: 9
tgtggccatt cacagtatgg ta    22

<210> SEQ ID NO 10
<211> LENGTH: 96
<212> TYPE: RNA
<213> ORGANISM: Homosapiens

<400> SEQUENCE: 10
cauguugacg gugagaggca ucauccgguu caucauuggc uucagcgcac ccauguccau    60
cguugcuguc aguuaugggc uuauugccac caagau    96

<210> SEQ ID NO 11
<211> LENGTH: 92
<212> TYPE: RNA
<213> ORGANISM: Homosapiens

<400> SEQUENCE: 11
ccccaaggcc aaccgcgaga agaugaccca gaucauguuu gagaccuuca acaccccagc    60
cauguacguu gcuauccagg cugugcuauc cc    92

<210> SEQ ID NO 12
<211> LENGTH: 93

```
<212> TYPE: RNA
<213> ORGANISM: Homosapiens

<400> SEQUENCE: 12
aaaaggggcu uugccuuugu aaccuuugac gaccaugacu ccguggauaa gauugucauu      60
cagaaauacc auacugugaa uggccacaac ugu                                  93
```

SYSTEM AND METHOD OF DETECTING RNAS ALTERED BY CANCER IN PERIPHERAL BLOOD

CROSS-REFERENCE TO RELATED APPLICATIONS

This application claims priority to U.S. Provisional Patent Application 61/584,097 filed on Jan. 6, 2012 and entitled SYSTEM AND METHOD OF DETECTING RNAS ALTERED BY CANCER IN PERIPHERAL BLOOD, the entirety of which is hereby incorporated by reference herein.

SEQUENCE LISTING

This application is being filed along with a sequence listing in Electronic format. The Sequence Listing is provided as a file entitled VIOMC_003A_SEQUENCE_LISTING.TXT, created Jan. 3, 2013, which is approximately 2 kb in size. The information in the electronic format of the sequence listing is incorporated herein by reference in its entirety in its entirety.

FIELD OF THE INVENTION

Systems and methods for detecting cancer by assaying extracts from patient blood are provided. In particular, methods for detecting circulating free RNA (cfRNA) levels and relationships that are highly specific to patients with certain cancers are provided.

BACKGROUND

Cancer is a major health risk in the United States and internationally. Treatments exist, but are often not administered to patients until the disease has progressed to a point at which treatment efficacy is compromised.

A major challenge in cancer treatment is to identify patients early in the course of their disease. This is difficult under current methods because early cancerous or precancerous cell populations may be asymptomatic and may be located in regions which are difficult to access by biopsy. Thus a robust, minimally invasive assay that may be used to identify all stages of the disease, including early stages which may be asymptomatic, would be of substantial benefit for the treatment of cancer.

SUMMARY OF THE INVENTION

The systems, devices, kits, and methods disclosed herein each have several aspects, no single one of which is solely responsible for their desirable attributes. Without limiting the scope of the claims, some prominent features will now be discussed briefly. Numerous other embodiments are also contemplated, including embodiments that have fewer, additional, and/or different components, steps, features, objects, benefits, and advantages. The components, aspects, and steps may also be arranged and ordered differently. After considering this discussion, and particularly after reading the section entitled "Detailed Description," one will understand how the features of the devices and methods disclosed herein provide advantages over other known devices and methods.

One embodiment is a method for detection of one or more RNA molecules in samples taken from a patient. In this embodiment, blood or blood component such as plasma is isolated from a patient suspected of having lung cancer or non-small cell lung cancer (NSCLC). The plasma is analyzed to measure the level of circulating free RNA (cfRNA) from one or more genes. In some embodiments the RNA to be measured is messenger ribonucleic acids (mRNA), such as mRNA from within the population of cfRNA in a patient's plasma. In some embodiments the level of circulating free actin beta (ACTB) RNA is measured. In some embodiments the level of circulating free HNRNPA1 RNA is measured. In some embodiments, the level of circulating free formylpeptide receptor gene (FPR1) RNA is measured. In some embodiments, the level of cfRNA from FPR1, as compared with the level of cfRNA from ACTB and HNRNPA1 is compared, as discussed below, to determine if a patient is at risk for having lung cancer or NSCLC. In some embodiments the NSCLC assayed is Stage I NSCLC.

In some embodiments, at least one subset of one or more RNAs (subset #2) is known to be present in plasma of cancer-free individuals in relatively consistent quantities, and is known to be present at a level different from this generally consistent level in individuals with cancer such as breast, colon or lung cancer. For example, levels may be consistently lower in, for example patients having non-small cell lung cancer (NSCLC), such as stage I NSCLC. In some embodiments levels may be consistently higher in patients having cancer, for example patients having non-small cell lung cancer (NSCLC), such as stage I NSCLC. In some embodiments the lung cancer of said individuals does not show metastasis to the lymph nodes. In some embodiments, the RNA(s) selected for subset #1 may be present in lower levels due to nuclease activity, and in some embodiments the RNA or region of the RNA assayed for may be highly sensitive to nucleases due to the presence of nuclease cleavage sites or the presence of secondary structures (i.e. double vs. single stranded) that are preferentially cleaved by RNases. In some embodiments the RNA selected for subset #1 may be represented in higher levels in certain cancer patients, such as lung cancer patients. In some embodiments, the change in levels of RNA accumulation in subset #1 may be due to effects of molecules secreted by cancers or immune cells within close proximity to tumors on other non-malignant tissues.

In some embodiment, RNAs in subset #1 are released into the blood at increased levels in cancer patients due to one or more of the following: 1) preferential release from cells into the blood, 2) increased abundance in tumor cells, 3) increased abundance in cells near the tumor (i.e. reactive cells or stroma), 4) increased abundance from cells not near the tumor, mediated by secreted signals.

Another subset of one or more RNAs (subset #2) may be known to be stably expressed in all individuals regardless of cancer status. In some embodiments, the RNAs in subset #2 are less sensitive to ribonucleases.

In some embodiments, relative abundance of markers of subset #1 and subset #2 may be indicative of the presence of cancerous cells, tumors, or cells with a heightened potential to become cancerous, and in other embodiments, the accumulation levels of markers in subset #1 alone may be indicative of cancerous cells, tumors, or cells with a heightened potential to become cancerous. In some embodiments the RNA levels of a subset #2 member or members may vary inversely with the levels of a subset #1 member or member, such that the ratio of the levels is indicative of cancer status.

In some embodiments, digital PCR or real-time PCR is used as a detection method to determine the presence or accumulation levels of RNA markers. In some embodiments, DNA sequencing may be used as a detection method to determine the quantity of RNA markers. In other embodiments, detection may occur by molecular barcoding technologies such as NanoString or nCounter.

In some embodiments, the results of RNA and/or DNA copy number are analyzed to determine an assay outcome (i.e., positive or negative result) based at least in part on statistical distances between results. In some aspects, patients may be classified into different risk groups based at least in part on the analysis of the relative abundance of markers as disclosed herein. The cumulative distribution function of the normal, binomial and/or Poisson distribution or similar functions may be used to determine relative abundance of RNAs. In some embodiments, the type of cancer present in a patient may be predicted at least in part on results of RNA expression.

BRIEF DESCRIPTION OF FIGURE DRAWINGS

Figure 1B:
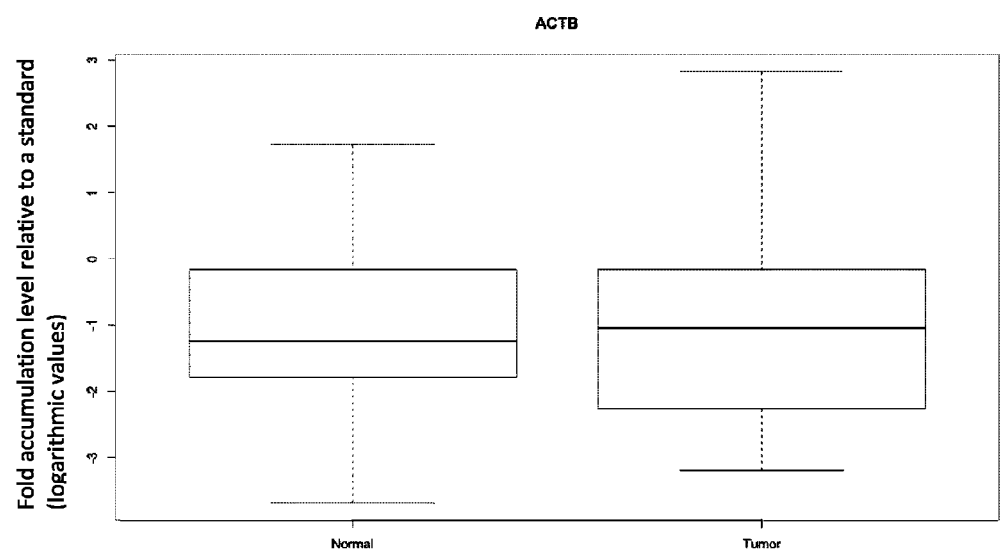
Figure 1C:
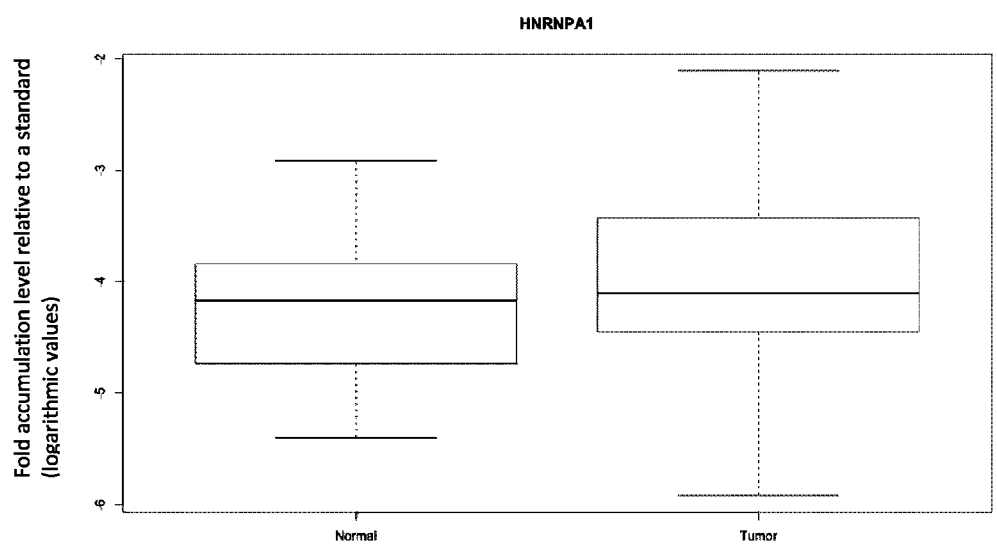

FIGS. 1A, 1B, and 1C depicts box plots of accumulation levels for the markers FPR1, ACTB and HNRNPA1, respectively, from plasma taken from normal individuals and individuals known to have one or more tumors. The y-axis indicates the transcript accumulation level per mL of plasma assayed, normalized against accumulation levels measured in Universal Human Reference RNA, represented natural logarithmically. According to the standard convention for boxplots, the central horizontal line in each column represents the median, the box represents the 25%-75% quartiles and the error bars indicate the extreme observations (excluding outliers). All units are ratios of transcript accumulation levels per mL of plasma assayed relative to accumulation levels of similar transcripts obtained from 1 ng of Agilent's Universal Human RNA.

Figure 2A:
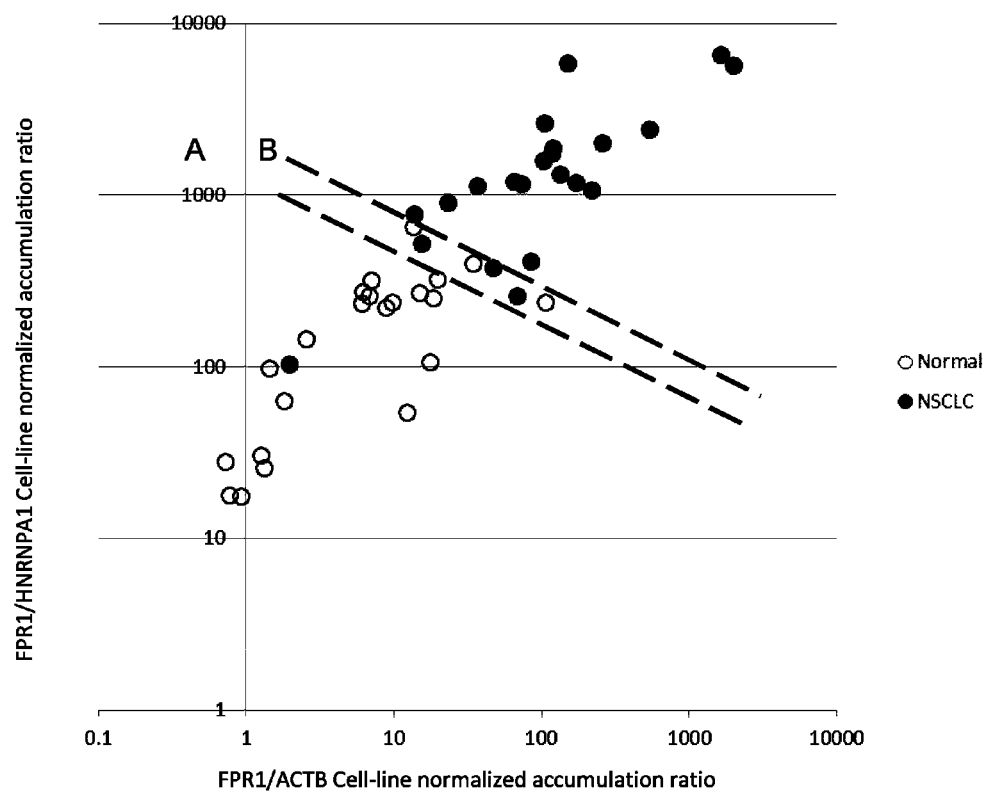

FIG. 2A depicts two-dimensional scatter-plots of ratios ACTB and HNRNPA1 values normalized to FPR1 values, wherein sample values are normalized to values determined from RNA obtained from a cell line control. Dashed line A separates the majority of values obtained from Normal patients. Dashed line B separates the majority of values obtained from NSCLC patients. The values between dashed lines A and B represent the minimal degree of overlap between the highest Normal values and the lowest NSCLC values.

Figure 2B:
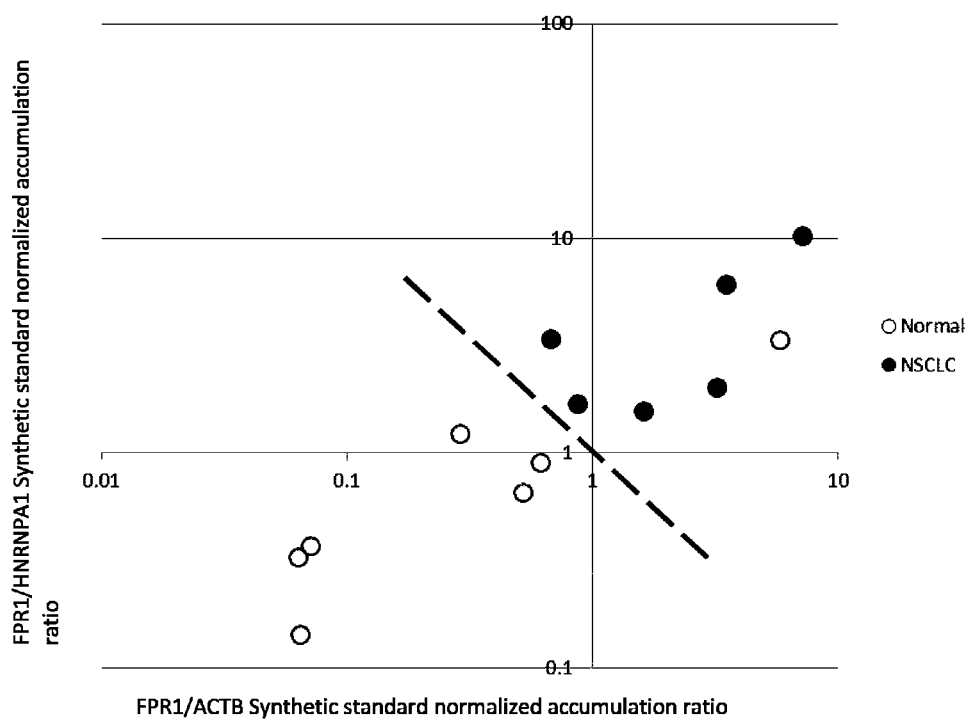

FIG. 2B depicts two-dimensional scatter-plots of ratios ACTB and HNRNPA1 values normalized to FPR1 values, wherein sample values are normalized to values determined from RNA obtained from a synthetic standard. The dashed diagonal line passing through the points (0.1, 10), (1, 1) and (10, 0.1) separates a population of normal samples (white-filled circles) from a population of predominantly NSCLC samples (black-filled circles).

DETAILED DESCRIPTION

One embodiment relates systems and methods for determining whether a patient at risk for cancer may have the disease by analyzing circulating nucleic acids in the blood. Determination of patients that may have cancer may be done on blood-derived specimens to assay RNA accumulation levels, and such analysis may be conducted by expression microarray, sequencing, nCounter, or real-time PCR. In some embodiments, expression levels of first subset of control nucleic acids are compared to expression levels of a second subset of nucleic acids that are known to be increased in patients having cancer. The first subset of control nucleic acids may be found by analyzing plasma from many disease-free patients and selecting genes that are expressed at stable levels within those patients. Subsets may also be found by analyzing solid tissue specimens taken from multiple tissue types (i.e. colon, lung, kidney, liver, etc.), and selecting genes that are expressed as circulating free nucleic acids at stable levels in a patient's blood.

In some embodiments, Subset #1 can be selected by analyzing genes whose transcript accumulation levels increase in plasma or in solid tumor specimens.

In some embodiments, Subset #1 includes genes whose circulating free nucleic acid levels decrease in plasma or in solid tumor specimens taken from individuals suffering from cancer.

In some embodiments, subset #1 comprises genes whose transcript accumulation levels are unchanged in normal individuals as compared to cancer patients. In these embodiments subset #2 is selected in combination with one or more genes of subset #1 whose accumulation levels increase in plasma or in solid tumors specimens.

In some embodiment, aspects of the invention relate to the discovery that circulating free RNA (cfRNA) levels of formylpeptide receptor gene (FPR1) RNA change in patients suffering from cancer. For example, cfRNA levels of FPR1 were found to increase in patients having lung cancer, as described below. Moreover, cfRNA levels of FPR1 were shown to increase in comparison to cfRNA levels of other genes, such as ACTB and HNRNPA1 or other transcripts listed in subset #2.

As shown in FIG. 1A and described with reference to Example 1, FIG. 1A depicts transcript accumulation levels for the gene FPR1 in samples measured from plasma taken from patients classified as having a cancer status as either normal (i.e., putatively cancer free) and tumor cells (i.e., having known tumor cells). The y-axis logarithmic values indicate that the FPR1 transcript accumulates on average at about a 100-fold greater level in tumor cell patients as compared to normal patients.

FIG. 1B and FIG. 1C depict transcript accumulation levels for the genes ACTB and HNRNPA1, respectively, in samples measured from plasma taken from patients classified as having a cancer status as either normal (i.e., putatively cancer free) and tumor cells (i.e., having known tumor cells). The y-axis logarithmic values indicate that the ACTB and HNRNPA1 transcripts accumulate on average at levels which are comparable in normal and in tumor cell patients.

In some embodiments, once subset #1 is known, subset #2 can be selected by analyzing a large number of candidates from multiple specimens and selecting those for which the difference between subset #2 and subset #1 is largest in plasma from cancer patients. In some embodiments, subset #2 can be selected by surveying transcript accumulation levels of many genes and finding which ones have the lowest variability. In some embodiments genes are selected not based on their individual accumulation levels but on the lack of change in their relative accumulation levels in cancer.

FIGS. 1A-C indicate that FPR1 and ACTB, FPR1 and HNRNPA1, or FPR1 and both ACTB and HNRNPA1 are suitable combinations of subset#1 and subset #2 genes for the methods disclosed herein, although embodiments of the invention are not limited to only these genes.

Once subset #1 (and subset #2 in some embodiments) are known within a given cancer type, the expression profile can be measured in plasma taken from cancer patients and patients for which a cancer is to be assayed. Because plasma can be collected and prepared within many primary care physician offices without posing any more risk than a standard blood draw, relative cfRNA accumulation levels between subsets #1 and subset #2 in some embodiments may be a valuable cancer biomarker. Additionally, if subsets #1 and subset #2 in some embodiments may be assayed reliably, they may have a number of advantages over current cancer assays. For example, in some embodiments this method may detect cancer at an early stage of development, cancer that poses few symptoms, cancer that is difficult to distinguish from benign conditions or cancer that may be developing in an area of the body that may not be accessible to traditional biopsy assays.

Increased RNase activity is often present in tumors. This RNase activity may inhibit tumor growth, and may be part of the immune system's response to cancer. Cytotoxic T cells may lead to apoptosis of cancer cells via IFN-γ, and this apoptosis may result in activation of RNases, such as RNase L. Death of cells via necrosis, which may be caused by hypoxia due to tumor growth, may also contribute to the release of RNases. It is known that plasma of lung cancer patients has increased RNase activity (Marabella et al., (1976) "Serum ribonuclease in patients with lung carcinoma," *Journal of Surgical Oncology*, 8(6):501-505; Reddi et al. (1976) "Elevated serum ribonuclease in patients with pancreatic cancer," *Proc. Nat'l. Acad. Sci. USA* 73(7):2308-2310). It is also known that lung cells contain RNases similar to those found in plasma (Neuwelt et al., (1978) "Possible Sites of Origin of Human Plasma Ribonucleases as Evidenced by Isolation and Partial Characterization of Ribonucleases from Several Human Tissues," *Cancer Research* 38:88-93).

When higher levels of RNase are present in plasma, any free RNA is susceptible to more rapid degradation. Thus, there may be less RNA detectable in plasma RNA preparations. While all RNA may be present at decreased levels, it is only possible to detect this difference with any level of accuracy when the normal variability of a gene is low. For example, if the normal range of a gene's expression is between 10 and 100 units, it may be difficult to accurately detect a decrease of 1 unit. However, if a gene's expression is normally between 10 and 11 units, a decrease of 1 unit is readily detectable (i.e. any number under 10 units would indicate a decrease).

FPR1 plays multiple roles in the lungs and cancer. FPR1 is expressed in lung fibroblasts (VanCompernolle et al. (2003) J Immunol. 171(4):2050-6) and is necessary for wound repair in the lungs (Shao (2011) Am J Respir Cell Mol Biol 44:264-269). It is known that fibroblasts are important in both attracting immune cells that fight the tumor (Gemperle (2012) PLOSOne 7(11):1-7, e50195) and creation of stroma which protects the tumor (Wang (2009) Clin Cancer Res 15(21) 6630-6638). FPR1 may also exacerbate the activity of other oncogenes in tumors (Huang (2007) Cancer Res 67(12): 5906-5913). There is no evidence that it is overexpressed in lung cancers, but FPR1 is known to be regulated by RNA stabilization (Mandal (2007) J Immunol 178:2542-2548, Mandal (2005) J Immunol 175:6085-6091). Given these roles, it is possible that FPR1 RNA is secreted deliberately by either tumor cells to enhance tumor growth (i.e. by activating wound-repair systems for growth or growing protective stroma) or immune cells to enhance the immune response (i.e. attracting additional immune cells).

In some embodiments the method can begin by extracting cfRNA from a patient's sample and assaying the cfRNA extracted. See, e.g., O'Driscoll, L. et al. (2008) "Feasibility and relevance of global expression profiling of gene transcripts in serum from breast cancer patients using whole genome microarrays and quantitative RT-PCR." Cancer Genomics Proteomics 5:94-104, which is hereby incorporated by reference in its entirety. In some embodiments, a consistent, repeatable method is used to isolate cfRNA from plasma or other source of RNA to ensure the reliability of the data. To obtain cfRNA from blood, one may use the protocol listed below although other methods are also contemplated.

cfRNA molecules may be purified from plasma or other samples using, for example, Qiagen's QIAamp circulating nucleic acid kit. The protocol in this kit is described in the document "QIAamp Circulating Nucleic Acid Handbook", Second Edition, January 2011, which is hereby incorporated by reference in its entirety. This protocol provides an embodiment of a method to purify circulating total nucleic acid from 1 mL of plasma. In brief, lysis reagents and proteases are added along with inert carrier RNA. The total nucleic acid (DNA and RNA) is bound to a column, and the column is washed multiple times then eluted off the column.

For example the protocol may be performed by executing the steps as follows. Pipet 100 µl, 200 µl, or 300 µl QIAGEN Proteinase K into a 50 ml centrifuge tube. Add 1 ml, 2 ml, or 3 ml of serum or plasma to the 50 ml tube. Add 0.8 ml, 1.6 ml, or 2.4 ml Buffer ACL (containing 1.0 µg carrier RNA). Close the cap and mix by pulse-vortexing for 30 s, making sure that a visible vortex forms in the tube. In order to ensure efficient lysis, mix the sample and Buffer ACL thoroughly to yield a homogeneous solution. The procedure should not be interrupted at this time.

To start the lysis incubation, incubate at 60° C. for 30 min. Place the tube back on the lab bench and add 1.8 ml, 3.6 ml, or 5.4 ml Buffer ACB to the lysate in the tube. Close the cap and mix thoroughly by pulse-vortexing for 15-30 seconds. Incubate the lysate-Buffer ACB mixture in the tube for 5 min on ice. Insert the QIAamp Mini column into the VacConnector on the QIAvac 24 Plus. Insert a 20 ml tube extender into the open QIAamp Mini column. Make sure that the tube extender is firmly inserted into the QIAamp Mini column in order to avoid leakage of sample.

Keep the collection tube for the dry spin, below. Carefully apply the lysate-Buffer ACB mixture into the tube extender of the QIAamp Mini column. Switch on the vacuum pump. When all lysates have been drawn through the columns completely, switch off the vacuum pump and release the pressure to 0 mbar. Carefully remove and discard the tube extender. Please note that large sample lysate volumes (about 11 ml when starting with 3 ml sample) may need up to 10 minutes to pass through the QIAamp Mini membrane by vacuum force. For fast and convenient release of the vacuum pressure, the Vacuum Regulator should be used (part of the QIAvac Connecting System). To avoid cross-contamination, be careful not to move the tube extenders over neighboring QIAamp Mini Columns.

Apply 600 µl Buffer ACW1 to the QIAamp Mini column. Leave the lid of the column open, and switch on the vacuum pump. After all of Buffer ACW1 has been drawn through the QIAamp Mini column, switch off the vacuum pump and release the pressure to 0 mbar. Apply 750 µl Buffer ACW2 to the QIAamp Mini column. Leave the lid of the column open, and switch on the vacuum pump. After all of Buffer ACW2 has been drawn through the QIAamp Mini column, switch off the vacuum pump and release the pressure to 0 mbar. Apply 750 µl of ethanol (96-100%) to the QIAamp Mini column. Leave the lid of the column open, and switch on the vacuum pump. After all of ethanol has been drawn through the spin column, switch off the vacuum pump and release the pressure to 0 mbar. Close the lid of the QIAamp Mini column. Remove it from the vacuum manifold, and discard the VacConnector. Place the QIAamp Mini column in a clean 2 ml collection tube, and centrifuge at full speed (20,000×g; 14,000 rpm) for 3 min.

Place the QIAamp Mini Column into a new 2 ml collection tube. Open the lid, and incubate the assembly at 56° C. for 10 min to dry the membrane completely. Place the QIAamp Mini column in a clean 1.5 ml elution tube (provided) and discard the 2 ml collection tube from step 14. Carefully apply 20-150 µl of Buffer AVE to the center of the QIAamp Mini membrane. Close the lid and incubate at room temperature for 3 min. Ensure that the elution buffer AVE is equilibrated to room temperature (15-25° C.). If elution is done in small volumes (<50 µl) the elution buffer has to be dispensed onto the center of the membrane for complete elution of bound DNA. Elution volume is flexible and can be adapted according to the requirements of downstream applications. The recovered eluate volume will be up to 5 µl less than the elution volume applied to the QIAamp Mini column. Centrifuge in a microcentrifuge at full speed (20,000×g; 14,000 rpm) for 1 min to elute the nucleic acids. The above example QIAamp Circulating Nucleic Acid Handbook 1/2011 is representative on knowledge of one of skill in the art and it illustrative rather than limiting. Alternate embodiments, including variants on the methods above or distinct approaches to cfRNA purification, are contemplated herein, and the methods and compositions disclosed herein are not limited to any particular cfRNA purification method.

Samples produced by this method may be highly pure and free of PCR inhibitors, and may be suitable for qPCR as used in some embodiments to assay cfRNA relative expression as an assay of, for example, various types of cancer.

In some embodiments the methods include performing PCR or qPCR in order to generate an amplicon. Numerous different PCR and qPCR protocols are known in the art and exemplified herein below and can be directly applied or adapted for use using the presently described compositions for the detection and/or identification of Some embodiments provide methods including Quantitative PCR (qPCR) (also referred as real-time PCR). qPCR can provide quantitative measurements, and also provide the benefits of reduced time and contamination. As used herein, "quantitative PCR" ("qPCR" or more specifically "real time qPCR") refers to the direct monitoring of the progress of a PCR amplification as it is occurring without the need for repeated sampling of the reaction products. In qPCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence (herein referred to as cycle threshold or "CT") varies directly with the concentration of amplifiable targets at the beginning of the PCR process, enabling a measure of signal intensity to provide a measure of the amount of target nucleic acid in a sample in real time.

Methods for setting up PCR and qPCR are well known to those skilled in the art. The reaction mixture minimally comprises template nucleic acid (e.g., as present in test samples, except in the case of a negative control as described below) and oligonucleotide primers and/or probes in combination with suitable buffers, salts, and the like, and an appropriate concentration of a nucleic acid polymerase. As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-3' direction along the template until synthesis terminates. An appropriate concentration includes one that catalyzes this reaction in the presently described methods. Known DNA polymerases useful in the methods disclosed herein include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase, FASTSTART™ Taq DNA polymerase, APTATAQ™ DNA polymerase (Roche), KLENTAQ 1™ DNA polymerase (AB peptides Inc.), HOTGOLDSTAR™ DNA polymerase (Eurogentec), KAPATAQ™ HotStart DNA polymerase, KAPA2G™ Fast HotStart DNA polymerase (Kapa Biosystemss), PHUSION™ Hot Start DNA Polymerase (Finnzymes), or the like.

In addition to the above components, the reaction mixture of the present methods includes primers, probes, and deoxyribonucleoside triphosphates (dNTPs).

Usually the reaction mixture will further comprise four different types of dNTPs corresponding to the four naturally occurring nucleoside bases, i.e., dATP, dTTP, dCTP, and dGTP. In some embodiments, each dNTP will typically be present in an amount ranging from about 10 to 5000 µM, usually from about 20 to 1000 µM, about 100 to 800 µM, or about 300 to 600 µM.

The reaction mixture can further include an aqueous buffer medium that includes a source of monovalent ions, a source of divalent cations, and a buffering agent. Any convenient source of monovalent ions, such as potassium chloride, potassium acetate, ammonium acetate, potassium glutamate, ammonium chloride, ammonium sulfate, and the like may be employed. The divalent cation may be magnesium, manganese, zinc, and the like, where the cation will typically be magnesium. Any convenient source of magnesium cation may be employed, including magnesium chloride, magnesium acetate, and the like. The amount of magnesium present in the buffer may range from 0.5 to 10 mM, and can range from about 1 to about 6 mM, or about 3 to about 5 mM. Representative buffering agents or salts that may be present in the buffer include Tris, Tricine, HEPES, MOPS, and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, for example, about pH 6.0, 6.5, 7.0, 7.5, 8.0, 8.5, 9.0, or 9.5. Other agents that may be present in the buffer medium include chelating agents, such as EDTA, EGTA, and the like. In some embodiments, the reaction mixture can include BSA, or the like. In addition, in some embodiments, the reactions can include a cryoprotectant, such as trehalose, particularly when the reagents are provided as a master mix, which can be stored over time.

In preparing a reaction mixture, the various constituent components may be combined in any convenient order. For example, the buffer may be combined with primer, polymerase, and then template nucleic acid, or all of the various constituent components may be combined at the same time to produce the reaction mixture.

Alternatively, commercially available premixed reagents can be utilized in the methods disclosed herein, according to the manufacturer's instructions, or modified to improve reaction conditions (e.g., modification of buffer concentration, cation concentration, or dNTP concentration, as necessary), including, for example, Quantifast PCR mixes (Qiagen), TAQMAN® Universal PCR Master Mix (Applied Biosystems), OMNIMIX® or SMARTMIX® (Cepheid), IQ™ Supermix (Bio-Rad Laboratories), LIGHTCYCLER® Fast-Start (Roche Applied Science, Indianapolis, Ind.), or BRILLIANT® QPCR Master Mix (Stratagene, La Jolla, Calif.).

The reaction mixture can be subjected to primer extension reaction conditions ("conditions sufficient to provide polymerase-based nucleic acid amplification products"), i.e., conditions that permit for polymerase-mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. As discussed below, in some embodiments, the amplification protocol does not include a specific time dedicated to annealing, and instead comprises only specific times dedicated to denaturation and extension. The number of reaction cycles will vary depending on the application being performed, but will usually be at least 15, more usually at least 20, and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture will usually be raised to, and maintained at, a temperature ranging from about 85 to 100° C., usually from about 90 to 98° C., and more usually from about 93 to 96° C., for a period of time ranging from about 3 to 120 sec, usually from about 3 sec.

Following denaturation, the reaction mixture can be subjected to conditions sufficient for primer annealing to template nucleic acid present in the mixture (if present), and for polymerization of nucleotides to the primer ends in a manner such that the primer is extended in a 5' to 3' direction using the nucleic acid to which it is hybridized as a template, i.e., conditions sufficient for enzymatic production of primer extension product. In some embodiments, the annealing and extension processes occur in the same step. The temperature to which the reaction mixture is lowered to achieve these conditions will usually be chosen to provide optimal efficiency and specificity, and will generally range from about 50 to 85° C., usually from about 55 to 70° C., and more usually from about 60 to 68° C. In some embodiments, the annealing conditions can be maintained for a period of time ranging from about 15 sec to 30 min, usually from about 20 sec to 5 min, or about 30 sec to 1 minute, or about 30 seconds.

This step can optionally comprise one of each of an annealing step and an extension step with variation and optimization of the temperature and length of time for each step. In a two-step annealing and extension, the annealing step is allowed to proceed as above. Following annealing of primer to template nucleic acid, the reaction mixture will be further subjected to conditions sufficient to provide for polymerization of nucleotides to the primer ends as above. To achieve polymerization conditions, the temperature of the reaction mixture will typically be raised to or maintained at a temperature ranging from about 65 to 75° C., usually from about 67 to 73° C. and maintained for a period of time ranging from about 15 sec to 20 min, usually from about 30 sec to 5 min. In some embodiments, the methods disclosed herein do not include a separate annealing and extension step. Rather, the methods include denaturation and extension steps, without any step dedicated specifically to annealing.

The above cycles of denaturation, annealing, and extension may be performed using an automated device, typically known as a thermal cycler. Thermal cyclers that may be employed are described elsewhere herein as well as in U.S. Pat. Nos. 5,612,473; 5,602,756; 5,538,871; and 5,475,610; the disclosures of which are herein incorporated by reference.

The methods described herein can also be used in non-PCR based applications to detect a target nucleic acid sequence, where such target may be immobilized on a solid support. Methods of immobilizing a nucleic acid sequence on a solid support are known in the art and are described in Ausubel et al, eds. (1995) Current Protocols in Molecular Biology (Greene Publishing and Wiley-Interscience, NY), and in protocols provided by the manufacturers, e.g., for membranes: Pall Corporation, Schleicher & Schuell; for magnetic beads: Dynal; for culture plates: Costar, Nalgenunc; for bead array platforms: Luminex and Becton Dickinson; and, for other supports useful according to the embodiments provided herein, CPG, Inc.

Variations on the exact amounts of the various reagents and on the conditions for the PCR or other suitable amplification procedure (e.g., buffer conditions, cycling times, etc.) that lead to similar amplification or detection/quantification results are known to those of skill in the art and are considered to be equivalents. In one embodiment, the subject qPCR detection has a sensitivity of detecting fewer than 50 copies (preferably fewer than 25 copies, more preferably fewer than 15 copies, still more preferably fewer than 10 copies, e.g. 5, 4, 3, 2, or 1 copy) of target nucleic acid in a sample.

In some embodiments the method may involve PCR amplification of cfRNA template RNA. A DNase treatment may be conducted to remove DNA contamination from RNA samples. cfRNA may be converted to cDNA with a reverse transcriptase and this step may use one or more of the same primers used within a PCR reaction. Target cDNAs may be amplified by, for example, a consistent, repeatable method to amplify cDNA from plasma or other cDNA. In some embodiments, one or more targets in cDNA may be amplified and quantified via Taqman chemistry. This protocol may not be the only suitable protocol to detect cfRNA quantity. However, it may be important to use a consistent protocol for cDNA synthesis and amplification, as variations in protocol may have a large effect on the eventual results.

In some embodiments the method may involve an assay for non-small cell lung cancers (NSCLC). In some embodiments, an assay may involve one or more of the following genes to comprise subset #2: PLGLB2, GABARAP, HNRNPA1, NACA, EIF1, UBB, UBC, CD81, TMBIM6, MYL12B, ACTB, HSP90B1, CLDN18, RAMP2, MFAP4, FABP4, MARCO, RGL1, ZBTB16, C10orf116, GRK5, AGER, SCGB1A1, HBB, TCF21, GMFG, HYAL1, TEK, GNG11, ADH1A, TGFBR3, INPP1, ADH1B; and one or more of the following genes to comprise subset #1: CTSS, FPR1, FPR2, FPRL1, FPRL2, CXCR2, NCF2.

A proprietary R1b assay may be used. In this embodiment, the assay may be a 3-plex qPCR assay that detects relative abundance of ACTB, HNRNPA1 and FPR1. In some embodiments ACTB and HNRNPA1 may fulfill the criteria for subset #2, and FPR1 may fulfill the criteria for subset #1.

In some embodiments, the subset #2 may consist of ACTB and subset #1 may consist of FPR1. In some embodiments the subset #2 may consist of HNRNPA1. In some embodiments the subset #2 may consist of ACTB and HNRNPA1. In some embodiments the subset #2 may comprise at least one of ACTB and HNRNPA1. In some embodiments subset #1 is FPR1 and Subset #2 is ACTB, or HNRNP1, or both ACTB and HNRNP1. In some embodiments, Qiagen assay #QF00119602 may be used for the qPCR, using the primers/probes provided accorded to the manufacturer's protocol.

Agilent's Universal RNA may be used as a standard in qPCR. In another embodiment, the R1b assay consisting of the following primer/probes may be as follows in Table 1.

TABLE 1

Amplification Primers

| Gene | Forward Primer | Probe | Reverse Primer |
|------|----------------|-------|----------------|
| FPR1 | TGACGGTGAGAGG CATCA (SEQ ID NO: 1) | [FAM] CGGTTCATCATTGGCTTCAG CGC [BHQ1] (SEQ ID NO: 2) | GGTGGCAATAAGCCCA TAACTG (SEQ ID NO: 3) |
| ACTB | AGGCCAACCGCGA GAAGA (SEQ ID NO: 4) | [CAL Fluor Gold 540] TGACCCAGATCATGTTTGAG ACCTTCA [BHQ1] (SEQ ID NO: 5) | TGCCATCCTAAAAGCC ACCCCA (SEQ ID NO: 6) |
| HNRNPA1 | GGGCTTTGCCTTTG TAACCTT (SEQ ID NO: 7) | [Quasar 705] TGACGACCATGACTCCGTGG ATA [BHQ3] (SEQ ID NO: 8) | TGTGGCCATTCACAGT ATGGTA (SEQ ID NO: 9) |

An RNA standard may be used to standardize result across multiple runs. This standard may be run at different dilutions. In some embodiments a synthetic standard may be used. For example, the normal ranges and cut-offs for one or more markers may be examined, and synthetic standards may be obtained and used directly, or diluted or combined such that they are at levels similar to predicted levels, such as predicted levels of the markers. In some embodiments the synthetic standards are present at levels that are at or within an order of magnitude of (i.e., 10-fold higher or 10-fold lower than) predicted levels in a patient sample. In some embodiments the synthetic standards are present at or within a difference of 5× (either 5-fold higher or five-fold lower) than levels predicted for a patient sample. In some embodiments the synthetic standards are present at or within a difference of 2× (either 2-fold higher or 2-fold lower) than levels predicted for a patient sample.

Many methods may be used to determine the appropriate level of each synthetic RNA in the synthetic standard. In one embodiment, one may run some number of samples representative of those and record the results (i.e. Ct value or fitted value to a standard). Each synthetic RNA may then be run on the same assay and the results may be measured on the same scale as the samples (i.e. Ct score or fitted value to a standard). Upon examination, one can determine which standards must be used. For example, 50 samples may be run and Ct scores ranging from 33-38 are obtained for a given gene. Standards of $10^7$, $10^6$, $10^5$, $10^4$, $10^3$, $10^2$ copies per µL may yield Ct scores of 24, 28, 32, 36, 40, or 44. Thus, it may be decided to use the $10^5$ standard, with dilutions to $10^4$ and $10^3$ conducted during assay setup. Using this strategy, only the original standard and two dilutions are needed to cover future samples. A similar method could be used to select appropriate concentrations for other standards in the same multiplex. Using this method, different concentrations may be used for each transcript to be assayed so a single standard can be used even if there are large discrepancies between different genes in the multiplex. By using the method disclosed herein, transcripts of widely ranging accumulation levels may be assayed with a reduced number of amplification reactions on standard templates.

For example, if one expects gene A to be in the range of 100 to 10,000 copies/µl and gene B to be in the range of 1,000,000 to 100,000,000 copies, one may create a mixed synthetic standard of 10,000 copies gene A and 100,000,000 copies gene B, thereby only requiring three standards in a 10-fold dilution series to cover the whole range expected for a sample. Using such a synthetic standard may in some embodiments dramatically reduce the number of standard or control samples that need to be run in a qPCR reaction plate to generate a standard curve that covers the expected ranges of both gene a and gene B. This method will also minimize risk of small errors introduced by pipetting from compounding during serial dilutions.

Regression may be used to fit data points generated from patient samples to the standard, such that results are expressed in standard units. In some embodiments, the standard consists of RNA created from one or more cell lines. In some embodiments, the standard may consist of synthetic RNAs. The number of fragments of each RNA within the standard may be known, and the standardized unit may be number of RNA molecules present for each target. In some embodiments, the standard may consist of the following synthetic RNAs:

| Target | Synthetic RNA sequence |
|--------|------------------------|
| FPR1 | 5'CAUGUUGACGGUGAGAGGCAUCAUCCGGUUCAUCAUUGGC UUCAGCGCACCCAUGUCCAUCGUUGCUGUCAGUUAUGGGCU UAUUGCCACCAAGAU3' (SEQ ID NO: 10) |
| ACTB | 5'CCCCAAGGCCAACCGCGAGAAGAUGACCCAGAUCAUGUUU GAGACCUUCAACACCCCAGCCAUGUACGUUGCUAUCCAGGC UGUGCUAUCCC3' (SEQ ID NO: 11) |
| HNRNPA1 | 5'AAAAGGGGCUUUGCCUUUGUAACCUUUGACGACCAUGACU CCGUGGAUAAGAUUGUCAUUCAGAAAUACCAUACUGUGAAU GGCCACAACUGU3' (SEQ ID NO: 12) |

Assays may involve components of different sequence or with different detectable labels targeted to similar regions, components targeted to different regions of the same genes, or components targeting the regions of genes other than those listed in the R1a assay above.

The results of an R1a test may be evaluated using the Decision Rules for Viomics' Test for cancer such as Viomics' NSCLC Test. A plot may be created where one axis is the ratio of FPR1 to ACTB, and the other axis is the ratio of FPR1 to HNRNPA1. An example of such a plot is indicated in FIGS. 2A-B. The plot in FIG. 2A is the initial data using a cell line control, and the plot in FIG. 2B is an independent data set that uses a synthetic standard.

When a cell line control is used, NSCLC and Normal Sample results are significantly different from one another. Despite the presence of some overlap, NSCLC samples consistently show ACTB to FPR1 ratios and HNRNPA1 to FPR1 ratios that are significantly greater than non-cancer samples when fit to a cell line control.

When a synthetic RNA standard rather than a cell line control is used, similar results are obtained but the degree of overlap is substantially decreased. This decreased overlap is due to decreased variability in the standards resulting from reduced numbers of serial dilutions (from 6 to 3). Each step of the serial dilution may introduce error. In FIG. 2B, a simple line can be drawn to separate all but one of the Normal synthetic standard result ratios from all of the NSCLC results.

The results may also be interpreted as a single ratio between a linear combination of the type #1 markers and a linear combination of the type #2 markers. A decision rule may state that any score above a given threshold indicates cancer, while a score below the threshold indicates the lack of cancer. A synthetic standard may be designed such that the coefficient on each marker is 1, such that the score is calculated as: Score=FRP1/(ACTB+HNRNPA1).

For example, transcript accumulation values for genes selected from the lists above may be determined from a sample and compared to levels determined from a set of synthetic standards (i.e. in a serial dilution series) that span the range of values that are typically obtained. For each gene, the transcript accumulation level determined from a patient sample is compared to the transcript accumulation level determined by performing a regression analysis on a synthetic standard template to fit the accumulation level values for each gene. The regression and fitted values are obtained for each gene individually. Additional analysis (i.e. calculating ratios) may be done once fitted values are obtained.

These scores may be compared to threshold values, such that scores above a threshold are indicative of a heightened risk of lung cancer as indicated by a patient sample.

It can be readily seen that, when this calculation is used with a threshold of ½, it is the same as using the line drawn in FIG. 2B. The correct concentrations for each standard, coefficients and threshold may be determined by collecting data on a small set of samples from both cancer and cancer-free patients, then using a linear model to separate them. The linear model may be generated via a statistical method such as logistic regression or support vector machines with a linear kernel function, or the linear model may be generated by inspection.

Exclusionary criteria may be implemented, such that any sample that meets the exclusionary criteria has no result reported. These exclusionary criteria may include other test preformed before or after one of the described embodiments. The exclusionary criteria may also be based on results of the test itself. For example, in some embodiments very low quantities of the markers indicate a degraded sample, and an unexpectedly large ratio between two accumulation levels such as those of ACTB and HNRNPA1, for example, may indicate that there is contamination. In some embodiments a sample is excluded if the ratio of ACTB to HNRNPA1 differs by more than 10, 5, 4, 3, or 2-folded compared to the median ratio of the accumulation levels of the genes. One example of a plausible contamination source is that of lymphocytes in the plasma sample.

In some embodiments the method may involve a Statistical Distance Determination. Because cfRNA from cancer cells may be highly diluted, a method may be required to determine significant changes in relative abundance. For this reason, in some embodiments, the method determines the assay outcome (i.e., positive or negative result) based on statistical distances between results as opposed to a fixed cutoff determined only through ROC curves.

Based on the specificity, the results may be divided into groups (high confidence, low confidence, etc.). This number may also be transformed by some simple formula to create a numerical score for confidence.

In some embodiments the method may involve Models and Derivations for predicting the type of cancer present in a patient based on results RNA expression in combination with demographic or lifestyle attribute(s).

In some embodiments cfRNA levels may be assayed using sequencing technology. Examples of sequencing technology include but are not limited to one or more technologies such as pyrosequencing, e.g., 'the '454' method (Margulies et al., (2005) *Genome sequencing in microfabricated high-density picolitre reactors.* Nature 437:376-380; Ronaghi, et al. (1996) *Real-time DNA sequencing using detection of pyrophosphate release.* Anal. Biochem. 242:84-89), 'Solexa' or Illumina-type sequencing (Fedurco et al., (2006), *BTA, a novel reagent for DNA attachment of glass and efficient generation of solid-phase amplified DNA colonies.* Nucleic Acid Research 34, e22; Turcatti et al. (2008), *A new class of cleavable fluorescent nucleotides: synthesis and optimization as reversible terminators for DNA sequencing by synthesis.* Nucleic Acid Research 36, e25), SOLiD sequencing technology (Shendure, J. et al. (2005) *Accurate multiplex polony sequencing of an evolved bacterial genome.* Science 309, 1728-1732; McKernan, K. et al, (2006) *Reagents, methods, and libraries for bead-based sequencing.* US patent application 20080003571), Heliscope Technology (Harris, T. D. et al. (2008) *Single-molecule DNA sequencing of a viral genome.* Science 320, 106-109), Ion Torrent Technology (Rothberg et al., (2011) *An integrated semiconductor device enabling non-optical genome sequencing.* Nature 475, 348-352), SMRT Sequencing Technology (Pacific Biosciences), or GridION nanopore-based sequencing (Oxford Nanopore Technologies; http://www.nanoporetech.com/technology/the-gridion-system/the-gridion-system). In some embodiments any number of so-called 'next generation' DNA sequencing methods may be used, as described in Shendure and Ji, "*Next-generation DNA sequencing*", Nature Biotechnology 26(10):1135-1145 (2008) or in other art available to one of skill in the art. Other methods for the determination of DNA sequence are also known in the art, and embodiments disclosed herein are not limited to any particular method of determining base identity at a particular locus to the exclusion of any other method.

In some embodiments, the cfRNA levels may be assayed via hybridization to a microarray, nCounter or similar. For example, one class of arrays commonly used in differential expression studies includes microarrays or oligonucleotide arrays. These arrays utilize a large number of probes that are synthesized directly on a substrate and are used to interrogate complex RNA or message populations based on the principle of complementary hybridization. Typically, these microarrays provide sets of 16 to 20 oligonucleotide probe pairs of relatively small length (20mers-25mers) that span a selected region of a gene or nucleotide sequence of interest. The probe pairs used in the oligonucleotide array may also include perfect match and mismatch probes that are designed to hybridize to the same RNA or message strand. The perfect match probe contains a known sequence that is fully complementary to the message of interest while the mismatch probe is similar to the perfect match probe with respect to its sequence except that it contains at least one mismatch nucleotide which differs from the perfect match probe. During expression analysis, the hybridization efficiency of messages from a sample nucleotide population are assessed with respect to the perfect match and mismatch probes in order to validate and quantitate the levels of expression for many messages simultaneously. In some embodiments an entire gene array is printed to a microarray. In some embodiments a subset of genes comprising FPR1 and at least one of ACTB and HNRNPA1 is included on a microarray. In some embodiments a microarray comprises at least FPR1, ACTB and HNRNPA1.

A device such as an nCounter, offered by Nanostring technologies, for example, may be used to facilitate analysis. An nCounter Analysis System is an integrated system comprising a fully automated prep station, a digital analyzer, the CodeSet (molecular barcodes) and all of the reagents and consumables needed to perform the analysis. Analysis on the nCounter system consists of in-solution hybridization, post-hybridization processing, digital data acquisition, and normalization in one simple workflow. In some embodiments the process is automated. In some embodiments custom or pre-designed sets of barcoded probes may be pre-mixed with a comprehensive set of system controls as part of said analysis.

A number of methods of and devices for obtaining the cfRNA transcript accumulation level data necessary to perform the methods and for use with the compositions and kits disclosed herein, and no single data accumulation method or device should be seen as limiting.

EXAMPLES

Example 1

Plasma was collected from patients known to have non-small cell lung cancer ("NSCLC") and patients without any known lung cancer (putatively "cancer free" individuals). There is some possibility that patients without any known lung cancer may in fact have an otherwise undetected cancer. The presence of these patients will lead to an over-estimation of the false positive rate for this test (because "false positives" from "healthy individuals" may in fact represent the presence of cancer in these individuals). After removing plasma that had obvious issues, such as orange color or turbidity, 25 cancer-free and 26 NSCLC plasma samples remained. The following stages of cancer were present from the 26 NSCLC patients: 8 stage I, 6 stage II, 5 stage III, and 7 stage unknown. The plasma was extracted with the QIAamp circulating nucleic acid kit (Qiagen #55114). The Quantifast Probe RT-PCR Plus Kit (Qiagen #204484) was used along with the previously described primers and probes for FPR1, ACTB, and HNRNPA1 to conduct quantitative Taqman PCR. Universal Human Reference RNA (Agilent #740000) was used as a standard, and regression was used to estimate quantities of each gene in the sample (FIG. 2A). Samples with a ratio of ACTB/HNRNPA1 above 75 were eliminated from the final results, and given a result of "no result". The following results were obtained. Note that the x-axis is the ratio of FPR1/ACTB and the Y-axis is the ratio of FPR1/HNRNPA1.

As shown in FIG. 1A, FPR1 median accumulation levels normalized against accumulation levels measured in Universal Human Reference RNA differed by about 100-fold between Normal and Tumor patient populations. Similarly, the upper limit of the 25% quartile of the Normal patent population was measurably below the lower limit 75% quartile of the measurements for the Tumor patient population. The highest, rarest extreme Normal measurements occasionally were as high as, but no higher than, the Tumor patient median values.

This result shows that measuring the circulating free RNA levels of FPR1 allows one to predict the presence of cancer in a patient.

As shown in FIG. 1B, ACTB median accumulation levels did not differ significantly between Normal and Tumor patient populations. There was also substantial overlap at the 25%-75% quartile range and among the extreme outliers in accumulation levels between Normal and Tumor patient populations.

Similarly, in FIG. 1C, HNRNPA1 median accumulation levels did not differ significantly between Normal and Tumor patient populations. There was also substantial overlap at the 25%-75% quartile range and among the extreme outliers in accumulation levels between Normal and Tumor patient populations.

This result demonstrates the suitability of ACTB and HNRNPA1 as subset #2 constituents or as reference standards.

As shown in FIG. 2A, when a cell line control was used, Tumor and Normal Sample results were significantly different from one another. Despite the presence of some overlap, NSCLC samples consistently showed FPR1 to ACTB ratios and FPR1 to HNRNPA1 ratios that were in general significantly greater than the corresponding values obtained for a cell line control.

This experiment shows that comparing the circulating free RNA levels of FPR1 to the circulating free RNA levels of HNRNPA1 or ACTB allows one to predict the presence of cancer in a patient.

Example 2

A second set of 6 NSCLC and 7 Normal patient samples were assayed using a protocol similar to that discussed in Example 1. Two technical modifications were made: plasma was extracted via the QIAsymphony DSP Virus/Pathogen Midi Kit (Qiagen 937055) and a synthetic standard as described above was used. Additional samples were excluded after a screen for obvious issues such as cloudiness or discoloration. The ratios of the fitted values for each gene were determined, and are shown in FIG. 2B. The X and Y axis are the same ratios as previously described.

As shown in FIG. 2B, when a synthetic standard was used, NSCLC and Normal Sample results were significantly different from one another. NSCLC samples consistently showed ACTB to FPR1 ratios and HNRNPA1 to FPR1 ratios that were significantly greater than the corresponding values obtained for plasma obtained from cancer-free individuals. A simple line can be drawn to separate all but one of the Normal synthetic standard result ratios from all of the NSCLC results.

While it may initially appear that there is a wider gap between the NSCLC and cancer-free group, this may be due to the smaller number of points. As fewer points are present, extreme values are less probable. Some reduction in variability may also be due to the smaller number of dilutions used creation of the synthetic standard. This is enabled by the ability to fine tune the concentration of each gene individually in the standard.

Example 3

Plasma was collected from a patient suspected of having lung cancer. FPR1, ACTB and HNRNPA1 transcript accumulation levels in the cfRNA population of said patient were determined from the patient's plasma as described above. Patient FPR1 accumulation levels were compared to levels known to correspond with healthy individuals and with individuals that have cancer, for example, the accumulation levels indicated in FIG. 1A. Other reference measures of FPR1 accumulation in cfRNA of healthy and cancer-positive individuals could also have been used. An arbitrary value of 100 was assigned to the full concentration of the standard for each gene, with the two additional dilutions used to create the standard curve being 10 and 1 arbitrary units. Sample 171 was collected from a patient known to have NSCLC. The values of 18.14, 26.64 and 5.38 were obtained for FPR1, ACTB and HNRNPA1 respectively. The score was calculated as 18.14/(26.64+5.38)=0.567 was obtained. Because this value is greater than 0.5, a positive result for NSCLC was obtained.

Plasma was collected from patient 164 with no evidence of cancer. Transcript accumulation levels of FPR1, ACTB and HNRNPA1 were obtained as above. The values of 3.53, 12.2 and 2.87 were obtained for FPR1, ACTB and HNRNPA1 respectively. The score is calculated as 3.53/(12.2+2.87)=0.234 was obtained. Because this value is less than 0.5, a negative result for NSCLC was obtained.

This experiment shows that determining the circulating free RNA levels of FPR1, ACTB and HNRNPA1 allows one to predict the presence of cancer, and particularly lung cancer, in a patient.

Example 4

Plasma is collected from a patient suspected of having lung cancer. FPR1 transcript accumulation levels in the cfRNA population of said patient are determined from the patient's plasma as described above. Patient FPR1 accumulation levels are compared to levels known to correspond with healthy individuals and with individuals that have cancer, for example, the accumulation levels indicated in FIG. 1A. Other reference measures of FPR1 accumulation in cfRNA of healthy and cancer-positive individuals may be used. Levels are found to be 60,000 FPR1 molecules per mL, which corresponds to the median accumulation level observed for Tumor patients but is at or above the extreme highest measured value for Normal patients.

This FPR1 accumulation level indicates with a high degree of confidence that a NSCLC cell population is present in the patient.

Plasma is collected from a second patient suspected of having lung cancer. FPR1 transcript accumulation levels in the cfRNA population of said patient are determined and compared as above. Levels are found to be 600 FPR1 molecules per mL, which corresponds to the median accumulation level observed for Normal patients but is at or below the extreme lowest measured value for Tumor patients. This FPR1 accumulation level indicates with a high degree of confidence that the patient is free of a cancerous or precancerous cell population detectable through this method.

This experiment shows that determining the circulating free RNA levels of FPR1 allows one to predict the presence of cancer in a patient.

What is claimed is:

1. A method of determining cancer risk in a person, comprising:
   providing a biological sample from a patient suspected of having cancer;
   contacting the biological sample with a probe specific for circulating free nucleic acids derived from a target formylpeptide receptor gene, wherein the presence of the circulating free nucleic acids in the biological sample creates probe-nucleic acid complexes specific for said target formylpeptide receptor gene;
   quantitating the level of said probe-nucleic acid complexes;
   normalizing the quantitated level of said probe-nucleic acid complexes against a synthetic quantification standard; and
   determining the patient's risk of having cancer associated with said target formylpeptide receptor gene, as indicated by an increase in the normalized level of the probe-nucleic acid complexes compared to reference levels in healthy persons.

2. The method of claim 1, wherein said target formylpeptide receptor gene is FPR1.

3. The method of claim 1, wherein the comparing comprises electronically comparing in a computer values reflective of said circulating free levels of said gene.

4. The method of claim 1, wherein the sample comprises blood components.

5. The method of claim 4, wherein the blood components comprise plasma.

6. The method of claim 1, wherein said synthetic quantification standard comprises template nucleic acids at concentrations within an order of magnitude of expected accumulation levels in a patient sample.

7. The method of claim 6, wherein said synthetic quantification standard comprises populations of template nucleic acids corresponding to at least two transcripts to be assayed in a patient sample, wherein each of the template nucleic acid populations is present at a concentration within an order of magnitude of an expected accumulation level of a corresponding transcript in a patient sample.

8. The method of claim 6, wherein the synthetic quantification standard comprises RNA extracted from a standard cell line.

9. The method of claim 1, wherein said quantitating comprises comparing said levels to the level of circulating free nucleic acids derived from a second gene that is known to be present at stable levels independent of cancer status.

10. The method of claim 1 wherein the cancer is lung cancer.

11. The method of claim 10 wherein the cancer is non-small cell lung cancer.

12. The method of claim 9 wherein the circulating free nucleic acids comprise circulating free ribonucleic acids.

13. The method of claim 12 wherein the circulating free nucleic acids comprise circulating free messenger ribonucleic acids (mRNA).

14. A method for determining lung cancer risk in a person, comprising the steps of:
   providing a sample comprising blood or blood components from a person suspected of having lung cancer;
   applying the biological sample to a nucleic acid analytical device, wherein said nucleic acid analytical device is programmed to detect the level of transcript derived from a target formylpeptide receptor gene in the sample;
   normalizing said detected level of transcript of said target formylpeptide receptor gene against a synthetic quantification standard;
   comparing the normalized level of transcript of said target formylpeptide receptor gene with at least one reference level of transcript of a second gene which has been normalized with the synthetic quantification standard;
   determining the person's risk of having a lung cancer associated with said target formylpeptide receptor gene, as indicated by the ratio of the normalized level of transcript derived from said target formylpeptide receptor gene to the normalized level of transcript of the reference gene.

15. The method of claim 14, wherein the sample comprises plasma.

16. The method of claim 14, wherein the target formylpeptide receptor gene is FPR1.

17. The method of claim 14, wherein said reference transcript level of said second gene comprises RNAs derived from Actin B (ACTB).

18. The method of claim 14, wherein said reference transcript level of said second gene comprises RNAs derived from HNRNPA1.

19. The method of claim 14, wherein said reference transcript level comprises RNAs derived from both ACTB and HNRNPA1.

20. The method of claim 14, wherein said synthetic quantification standard comprises template nucleic acids at concentrations within an order of magnitude of expected accumulation levels in a patient sample.

21. The method of claim 20, wherein said synthetic quantification standard comprises populations of template nucleic acids corresponding to at least two transcripts to be assayed in a patient sample, and wherein each of said template nucleic acid populations is present at a concentration within an order of magnitude of an expected accumulation level of a corresponding transcript in a patient sample.

22. The method of claim 21, wherein said synthetic quantification standard comprises at least three synthetic nucleic acid molecules having the nucleotide sequences set forth in SEQ ID NO: 10, SEQ ID NO: 11, and SEQ ID NO: 12, respectively.

23. A method for determining cancer risk in a person, comprising the steps of:

providing a sample comprising blood or blood components from a patient suspected of having cancer;

applying the biological sample to a nucleic acid analytical device, wherein said nucleic acid analytical device is programmed to detect a level of circulating free nucleic acids derived from a HNRNPA1 gene in the sample;

normalizing the detected level of circulating free nucleic acids derived from the HNRNPA1 gene with a synthetic quantification standard; and comparing the normalized level of circulating free nucleic acids derived from the HNRNPA1 gene with a level of circulating free nucleic acids derived from a second transcript, wherein the level of circulating free nucleic acids derived from the second transcript indicates said cancer risk.

24. The method of claim 23, wherein said cancer risk is further defined as the presence of cancer, or of precancerous cells, in said patient.

25. The method of claim 24, wherein said second transcript is FPR1.

26. A method for evaluating the quality of a plasma-derived nucleic acid sample comprising the steps of:
 a) contacting the nucleic acid sample with a probe specific for ACTB transcript to generated probe-ACTB transcript complexes;
 b) contacting the nucleic acid sample with a probe specific for HNRNPA1 to generate probe-HNRNPA1B transcript complexes;
 c) quantitating the levels of the probe-ACTB transcript complexes and probe-HNRNPA1B transcript complexes generated from step (a) and (b), respectively;
 d) normalizing the quantitated levels of the probe-ACTB transcript complexes and probe-HNRNPA1B transcript complexes with a synthetic quantification standard; and
 e) discarding said sample if said normalized levels differ by greater than five times the median ratio between the genes.

27. The method of claim 1 or 14, wherein said cancer risk is further defined as the presence of cancer, or of precancerous cells, in said person.

28. The method of claim 27, further comprising treating said person for said cancer.

29. The method of claim 23, wherein said cancer is lung cancer.

30. The method of claim 29, wherein said cancer is non-small cell lunch cancer.

* * * * *